US009599806B2

(12) United States Patent
Zhong et al.

(10) Patent No.: US 9,599,806 B2
(45) Date of Patent: Mar. 21, 2017

(54) SYSTEM AND METHOD FOR AUTOFOCUSING OF AN IMAGING SYSTEM

(71) Applicant: General Electric Company, Schenectady, NY (US)

(72) Inventors: Zhangyi Zhong, Palo Alto, CA (US); Chun Zhan, Niskayuna, NY (US); Kang Zhang, Niskayuna, NY (US); Daniel Curtis Gray, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 14/734,320

(22) Filed: Jun. 9, 2015

(65) Prior Publication Data

US 2016/0363755 A1    Dec. 15, 2016

(51) Int. Cl.
| | | |
|---|---|---|
| *G02B 21/00* | (2006.01) | |
| *G02B 21/24* | (2006.01) | |
| *G02B 7/28* | (2006.01) | |
| *G01B 9/02* | (2006.01) | |

(Continued)

(52) U.S. Cl.
CPC ....... *G02B 21/245* (2013.01); *G01B 9/02004* (2013.01); *G01B 9/02091* (2013.01); *G01N 21/8851* (2013.01); *G01N 21/9501* (2013.01); *G02B 7/28* (2013.01); *G02B 21/0016* (2013.01); *G01N 2201/127* (2013.01)

(58) Field of Classification Search
CPC .... G02B 21/245; G02B 7/28; G02B 21/0016; G01B 9/02004; G01B 9/02091; G01N 21/8851; G01N 21/9501; G01N 2201/127

USPC .................................................. 359/368, 383
See application file for complete search history.

(56) References Cited

U.S. PATENT DOCUMENTS

| | | | | |
|---|---|---|---|---|
| 5,338,924 A | * | 8/1994 | Barrett ..................... | G02B 7/28 250/201.4 |
| 5,438,413 A | * | 8/1995 | Mazor ................. | G03F 7/70633 356/400 |

(Continued)

FOREIGN PATENT DOCUMENTS

| | | |
|---|---|---|
| WO | 2011059679 A1 | 5/2011 |
| WO | 2012018796 A3 | 2/2012 |
| WO | 2014139023 A1 | 9/2014 |

OTHER PUBLICATIONS

Finke et al., "Motorization of a surgical microscope for intra-operative navigation and intuitive control", The International Journal of Medical Robotics and Computer Assisted Surgery, vol. 6, (2010), pp. 269-280.

*Primary Examiner* — Frank Font
(74) *Attorney, Agent, or Firm* — Pabitra K. Chakrabarti

(57) ABSTRACT

Methods and systems for autofocusing of an imaging system are presented. Provided is an imaging system and an optical interferometry system for generating one or more images corresponding to a target region in a subject. The method provides calibration information that identifies a focal position of the optical interferometry system corresponding to a determined focal position of the imaging system. A subsequent focal position of the imaging system is determined for generating a desired image corresponding to at least one of another target region in the subject and another position of the target region relative to the imaging system based on the calibration information.

12 Claims, 13 Drawing Sheets

(51) Int. Cl.
*G01N 21/95* (2006.01)
*G01N 21/88* (2006.01)

(56) References Cited

U.S. PATENT DOCUMENTS

| | | | |
|---|---|---|---|
| 5,768,401 A * | 6/1998 | Csipkes | G02B 6/3843 |
| | | | 382/255 |
| 6,004,314 A | 12/1999 | Wei et al. | |
| 6,603,529 B1 * | 8/2003 | Finarov | G03F 7/70058 |
| | | | 355/27 |
| 7,071,451 B2 | 7/2006 | Ishikawa et al. | |
| 7,538,564 B2 | 5/2009 | Ehrmann et al. | |
| 7,576,307 B2 | 8/2009 | Yazdanfar et al. | |
| 7,901,080 B2 | 3/2011 | Hauger et al. | |
| 8,218,840 B2 | 7/2012 | Eisfeld et al. | |
| 8,619,264 B2 | 12/2013 | Randers-Pehrson et al. | |
| 2002/0180986 A1 * | 12/2002 | Nikoonahad | G03F 7/70625 |
| | | | 356/600 |
| 2004/0235205 A1 * | 11/2004 | Levy | G01N 21/211 |
| | | | 438/14 |
| 2010/0059657 A1 * | 3/2010 | Smith | G01N 21/211 |
| | | | 250/201.2 |
| 2010/0172020 A1 * | 7/2010 | Price | G02B 21/0016 |
| | | | 359/381 |
| 2011/0134308 A1 * | 6/2011 | Arnz | G02B 21/245 |
| | | | 348/345 |
| 2013/0123641 A1 * | 5/2013 | Goldfain | A61B 5/0066 |
| | | | 600/476 |
| 2013/0342902 A1 * | 12/2013 | Krueger | G02B 21/242 |
| | | | 359/383 |
| 2014/0293278 A1 * | 10/2014 | Smith | G01B 11/0608 |
| | | | 356/300 |
| 2015/0294468 A1 * | 10/2015 | Shimizu | A61B 3/12 |
| | | | 356/479 |

* cited by examiner

SYSTEM AND METHOD FOR AUTOFOCUSING OF AN IMAGING SYSTEM

BACKGROUND

Embodiments of the present specification relate generally to diagnostic imaging systems, and more particularly to systems and methods for autofocusing a digital microscope via use of optical coherence tomography (OCT).

Digital optical microscopes are used to observe a wide variety of samples such as biological tissues on histopathologic slides for archiving, telepathology, and/or rapid information retrieval. Generally, the digital microscopes may include high resolution objective lenses having small depths of focus to aid in generation of sharp images corresponding to a target region in a selected sample. However, such a tight depth of focus necessitates that the target region be closely aligned to a focal point of an associated objective lens.

Accordingly, in a conventional digital microscope, the sample may be repeatedly repositioned along an axial Z dimension to focus and/or locate an optimal imaging position. Specifically, the conventional microscope may perform autofocusing by obtaining multiple images at multiple focal distances, determining quantitative characteristics for each image, determining an optimal focal distance based on the quantitative characteristic, and using a feedback loop to adjust the focal distance for imaging the target region.

However, such repeated repositioning of the sample and/or a multiple image acquisitions may create time delays that prevent rapid autofocusing during diagnostic procedures. For example, a biomarker multiplexing process may entail tissue preparation, staining, bleaching, and/or imaging the target region for determining relevant clinical indicators. Although, the tissue preparation, staining, and bleaching may be batch-processed, slide scanning based on fluorescence imaging still remains a bottleneck on an overall processing time, thus impeding expedited and/or real-time diagnosis and/or treatment of a patient. Similarly, an inability to rapidly autofocus may also impede other automated biological and biomedical applications such as high-throughput pharmaceutical screening and/or large-scale autonomous cell manipulation. An inability to accurately autofocus may also hinder performance of non-medical imaging applications such as integrated circuit chip inspection and/or microassembly of hybrid microelectromechanical systems (MEMS).

Accordingly, certain conventional digital microscopes employ laser-based focusing systems for automatically focusing on the target region. Specifically, the laser-based auto-focusing systems perform autofocusing by directing a laser beam at the sample, measuring a reflection of the laser beam off the sample to provide a single reference point, and using a feedback loop to adjust the focal distance. Although the laser-based focusing approach provides autofocusing, the single reference point may lack sufficient information for accurate autofocusing. Particularly, the laser-based focusing approach may merely provide sufficient information to locate glass interfaces such as the coverslip and slide below. However, when using the laser-based focusing approach, the sample itself may provide only a weak and non-repeatable signal that may not be sufficient to determine an accurate location of the sample even when using a known offset from the coverslip or slide to the sample.

BRIEF DESCRIPTION

In accordance with aspects of the present specification, an autofocusing method is disclosed. The method includes providing an imaging system and an optical interferometry system for generating one or more images corresponding to a target region in a subject. The method further includes determining calibration information that identifies a focal position of the optical interferometry system corresponding to a determined focal position of the imaging system at which the imaging system generates a desired image of the target region at an initial position. Moreover, the method includes determining a subsequent focal position of the imaging system for generating a desired image corresponding to at least one of another target region in the subject and another position of the target region relative to the imaging system based on the calibration information. Additionally, the method includes autofocusing the imaging system using the subsequent focal position to generate the desired image corresponding to at least one of the another target region in the subject and another position of the target region relative to the imaging system.

In accordance with aspects of the present specification, an autofocusing system is disclosed. The system includes an imaging system configured to image a target region in a subject. The system further includes an optical interferometry system operatively coupled to the imaging system, wherein the optical interferometry system is configured to generate one or more axial images of the target region. Additionally, the system includes a computing device communicatively coupled to one or more of the imaging system and the optical interferometry system. Particularly, the computing device is configured to determine calibration information that identifies an initial focal position of the optical interferometry system corresponding to a determined focal position of the imaging system at which the imaging system generates a desired image of the target region. Further, the computing device is also configured to determine a subsequent focal position of the imaging system for generating a desired image corresponding to at least one of another target region in the subject and another position of the target region relative to the imaging system based on the calibration information. Additionally, the system includes a positioning subsystem configured to move the target region to the another position relative to the imaging system at which the imaging system is configured to generate a desired image of the repositioned target region using the subsequent focal position, wherein the positioning subsystem is operatively coupled to one or more of the imaging system and the optical interferometry system.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
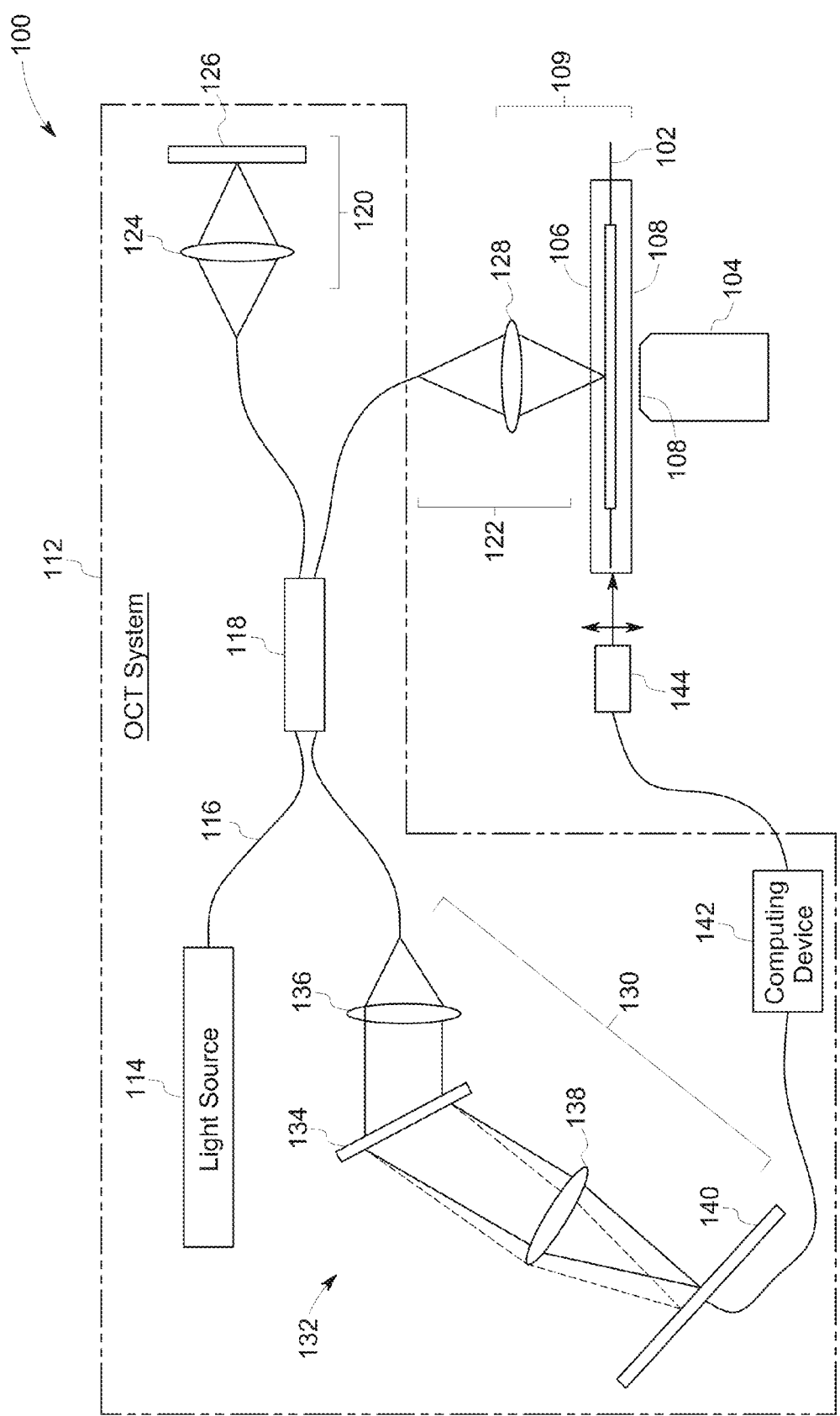
FIG. 1 is a block schematic diagram of an exemplary system that provides rapid autofocusing for imaging a target region or a sample, in accordance with aspects of the present specification.

The following description presents systems and methods for high speed, high axial resolution, and repeatable auto focusing of an imaging system that does not require repeated repositioning and/or imaging of an object of interest. Particularly, the embodiments described herein disclose systems and methods that allow for auto-focusing on the object of interest such as a biological or non-biological sample via use of an interferometer such as an optical coherence tomography (OCT) system.

Generally, OCT is based on low temporal coherence interferometry and is often implemented using a Michelson interferometer. Typically, an OCT imaging signal originates from measurement of small changes in an index of refraction corresponding to highly transparent media. Accordingly, OCT may be particularly well suited for locating an accurate location of the sample disposed within a glass slide as the slide may be considered to be a stack of clear optical interfaces. Particularly, the OCT may be used to generate one or more sub-micrometer resolution cross-sectional images that may be indicative of an axial location of the sample between the slide and a corresponding cover glass.

Typically, the cross sectional OCT images may be obtained more than 30,000 times per second, thus providing sufficient axial location information to compute appropriate positioning offsets for rapid and automatic focusing of the imaging system on a desired region of the sample. Thus, the OCT images may be used to determine optimal focal positions of subsequently available samples without a need for repeated image data acquisition and/or processing. Furthermore, a focusing motor may be configured to use the axial location information to move a subsequent slide quickly and accurately to a corresponding optimal focal position, thus allowing for a stable imaging setup and saving considerable imaging time. As used herein, the term "optimal focal position" may be used to refer to a focal position of the associated imaging system that allows for generation of images that satisfy a desired quality metric such as signal-to-noise ratio (SNR).

For the purpose of discussion, the present embodiments are described with reference to an OCT-assisted digital microscope employed for imaging a biological sample without moving the sample or an associated optical objective element. However, it may be appreciated that embodiments of the present systems and methods may be used in other medical and non-medical imaging applications. By way of example, the embodiments described herein may be used in the semiconductor industry for providing super-resolution imaging systems for fast and accurate wafer/reticle inspection. In another example, the embodiments of the present systems and methods may be used for rapid and accurate focusing during in vivo imaging of brain tissues in live animals to minimize corresponding image motion artifacts. An exemplary environment that is suitable for use of various embodiments of the present systems and methods is described in the following sections with reference to FIG. 1.

FIG. 1 illustrates an exemplary autofocusing system 100 that provides rapid autofocusing for imaging a target region or a sample 102 corresponding to a subject such as a patient, an industrial object, and/or baggage. In one embodiment, the system 100 may further include a primary imaging system 104 configured to generate one or more images of the sample 102 at a desired resolution. Accordingly, the primary imaging system 104, for example, may include an optical microscope, a digital microscope, a telescope, a charge coupled device, a camera, or any other suitable imaging system. However, for clarity, an embodiment of the imaging system 104 is described with reference to a digital microscope (microscope 104). In one embodiment, the microscope 104 may be configured to image the sample 102 that may be mounted between a coverslip 106 and a slide interface 108 of a slide 109 disposed on a stage 110 of the microscope 104.

As previously noted, conventional microscopes have small depths of focus that necessitate the target region to be closely aligned to a focal point of an associated objective lens. A depth of focus of a microscope is indicative of a range in which a target object may be considered to be in a desired focus in an axial Z dimension corresponding to the microscope. Typically, a depth of focus of conventional microscopes range from about 0.7-3 microns that necessitates the target region to be closely aligned to a focal point of an objective lens in the microscopes. Accordingly, in conventional microscopes, a sample is repeatedly repositioned to focus and/or locate an optimal imaging position. However, such repeated repositioning of the sample and/or a multiple image acquisitions may create time delays that prevent rapid autofocusing during diagnostic procedures.

Accordingly, the system 100 includes an optical interferometer 112 configured to acquire axial scans of targets with varying refractive index to aid in directly, rapidly, and repetitively measuring a precise location of the sample 102 mounted on the stage 110 of the microscope 104. In one embodiment, the optical interferometer may correspond to an OCT system (OCT system 112) configured to generate cross-sectional images that may be used to determine a relative axial location of the sample 102 within the coverslip 106 and the slide interface 108 disposed on the microscope stage 110. For purposes of discussion, the OCT system 112 is described in the context of a spectral or Fourier-domain OCT system. However, it may be appreciated that other frequency domain, time-domain or swept-source OCT systems having free space or fiber-based layouts may be used substantially similarly in the system 100 to auto-focus on the sample 102.

According to certain aspects of the present specification, the OCT system 112 may include a light source 114 having broad bandwidth and short low-coherence length. Specifically, the light source 114 having a wide spectrum of wavelength, for example from visible band to infrared band, may be selected for imaging the sample 102. Accordingly, the light source 114 may include devices such as superluminescent diodes (SLDs), ultrashort pulsed lasers, supercontinuum lasers, vertical cavity emitting lasers (VCELs), swept source lasers, light emitting diodes, and/or conventional lamp light sources. In a presently contemplated embodiment, a relatively cost-effective SLD is used as the light source 114 to achieve broadband light with relatively high power. Further, collimated light generated from a PN-junction inside the SLD is amplified through an optical wave guide 116 and coupled into a free space or fiber-based beam splitter and/or coupler 118 to appropriately illuminate the sample 102.

Specifically, in one embodiment, the beam splitter and/or coupler 118 splits the collimated light into a first and second set of light beams towards a reference channel 120 and a sample channel 122, respectively. In certain embodiments, a polarization controller (not shown) may be used to balance a state of polarization of the light in the reference channel 120 and the sample channel 122. In an exemplary implementation, the reference channel 120, for example, includes an achromatic focusing lens 124 and a silver-coated mirror 126 that reflect back the first set of light beams back towards the beam splitter and/or couple 118. In addition, the reference channel 120 may also include a variable neutral density filter (not shown) to adjust reflected power to achieve desired interference with the second set of light beams that are incident on and are reflected back from the sample 102.

Further, the sample channel 122, for example, includes an objective lens 128 that focuses the second set of light beams on to the sample 102 mounted on the microscope stage 110. The second set of light beams interacts with the sample 102, which reflects a small portion of the light beams back towards the beam splitter and/or coupler 118. The beam splitter and/or coupler 118, in turn, combines the light beams reflected from the sample channel 122 and the reference channel 120, thereby resulting in an interference pattern in a detection channel 130.

According to certain aspects of the present specification, the spectral domain OCT system 112 is configured to collect all of the wavelengths of light in the interference pattern at the same time using a specially designed spectrometer 132. Judicious design of the spectrometer 132 allows the OCT system 112 to provide exceptional images for a wide range of research and clinical applications. An exemplary design of the spectrometer 132 used in the OCT system 112 will be described in greater detail with reference to FIG. 2.

In a presently contemplated embodiment, the spectrometer 132 includes a grating 134, a plurality of lenses 136 and 138, and a detector 140 to detect a modulation signal resulting from the interference pattern. Particularly, in certain embodiments, the grating 134 may be configured to separate interfering light beams that are reflected from the sample channel 122 and the reference channel 120 to detect the resulting modulation signal. Accordingly, a transmission grating having a relatively flat spectral response and high diffraction efficiency for the near infrared (NIR) spectrum may be employed to maximize an SNR of detection. In one implementation, for example, the grating 134 may be selected so as to have a frequency of about 1200 lines per minute and more than about 70% diffraction efficiency for the NIR spectrum.

Figure 2:
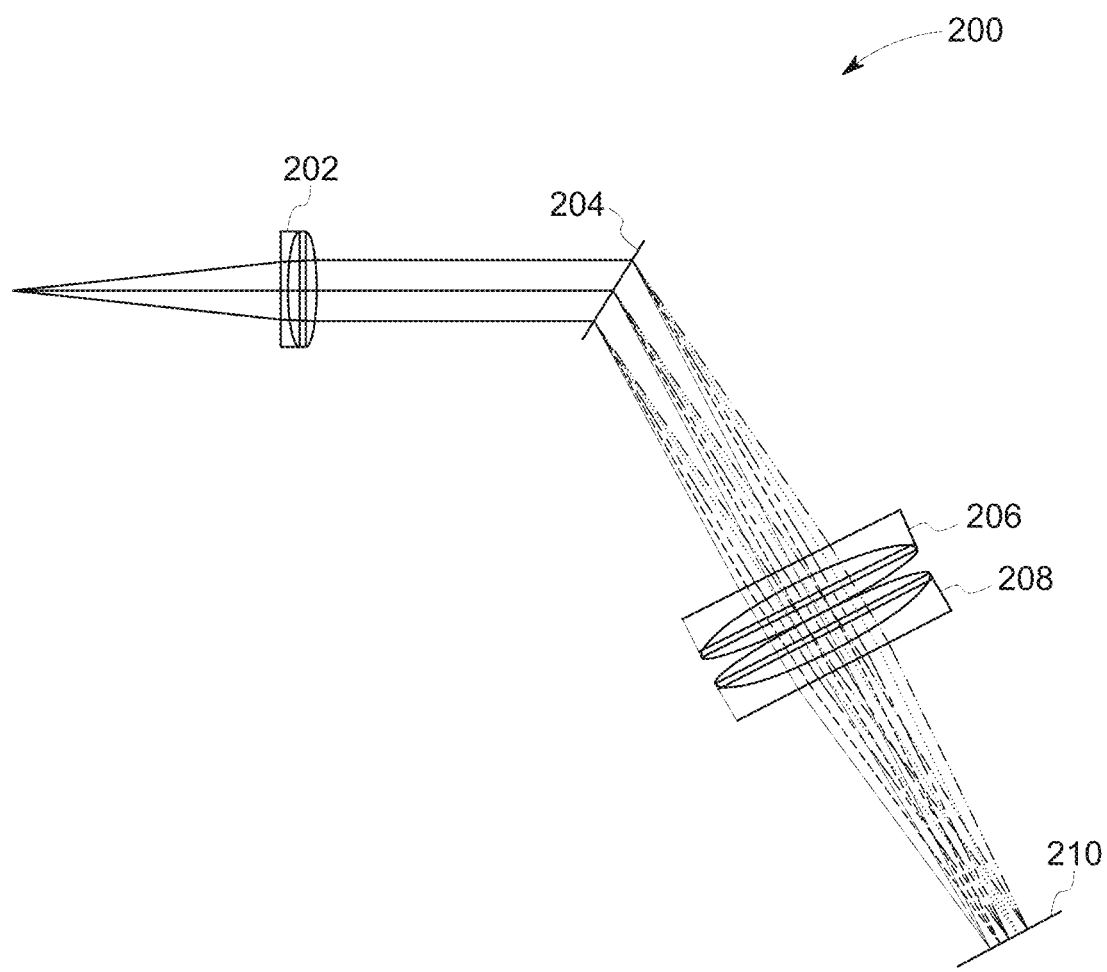
FIG. 2 is an exemplary schematic diagram of a desired spectrometer that may aid in optimal collimation and focusing of the light beams in the system of FIG. 1, in accordance with aspects of the present specification.

Generally, sensitivity of a spectral domain OCT system such as the OCT system 112 depends upon efficient design of the spectrometer 132. For example, a focus spot size at the detector 140 in the spectrometer is selected to be within a specified pixel size of the detector 140 to avoid a fall in sensitivity of the OCT system 112. The smaller focal spot size may also allow for generation of a higher modulation signal and high SNR OCT images. Additionally, the spectrometer 132 may include achromatic doublets in the near IR spectrum band to minimize an influence of dispersion. FIG. 2, for example, depicts an example of a spectrometer design that may be employed in the OCT system 112.

Specifically, FIG. 2 shows an exemplary schematic diagram of a desired spectrometer 200 that may aid in optimal collimation and focusing of the light beams. In one embodiment, the spectrometer 200 may include a 1 inch 60 millimeter (mm) achromatic doublet 202 that may be configured to use the entire surface of an associated grating 204. Additionally, two 2 inch 150 mm achromatic doublets 206 and 208 may be combined to focus the light beams emanating from the grating 204 onto a data acquisition unit such as a detector 210. In one embodiment, the detector 210 may include a charge-coupled device (CCD) and/or a camera having one row of 2048 pixels with a pixel size of about 10 micrometer (um). Use of a combination of two focusing doublets 206 and 208 in the spectrometer 200 effectively minimizes aberrations during a focusing process, thereby aiding in enhanced OCT imaging of the subject as compared to a conventional spectrometer. A comparison of the source spectrum measurements obtained by a conventional spectrometer and measurements obtained by the spectrometer 200 are depicted in FIGS. 3-4.

Figure 3:
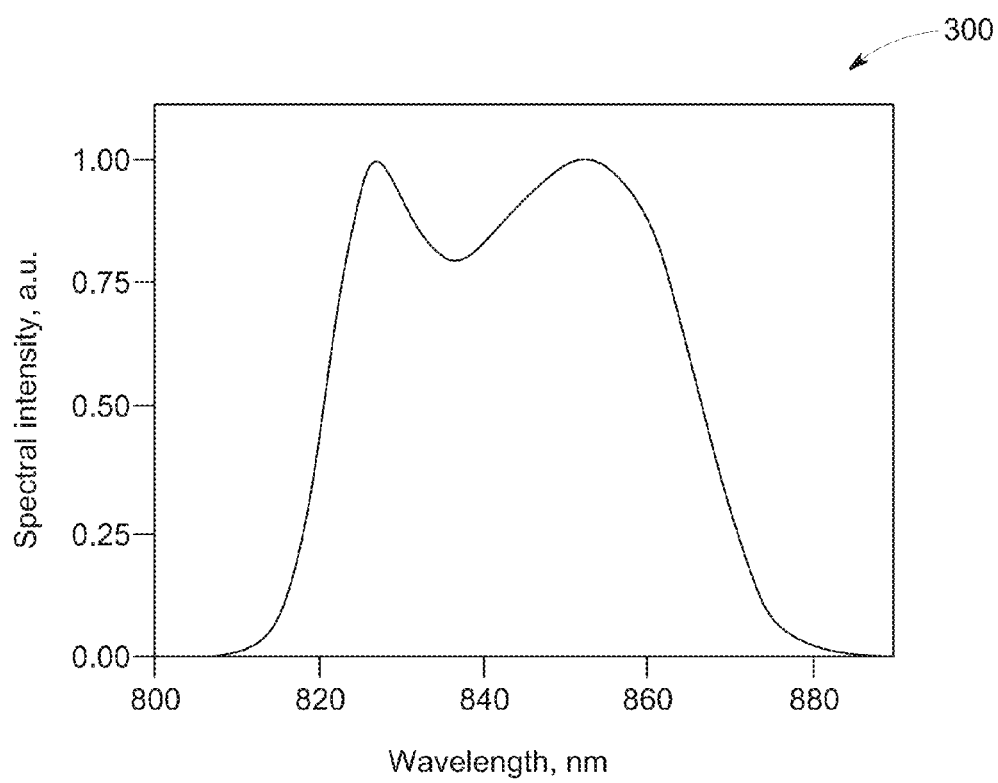
FIG. 3 is a graphical representation depicting a source spectrum measurements obtained using a conventional spectrometer.
Figure 4:
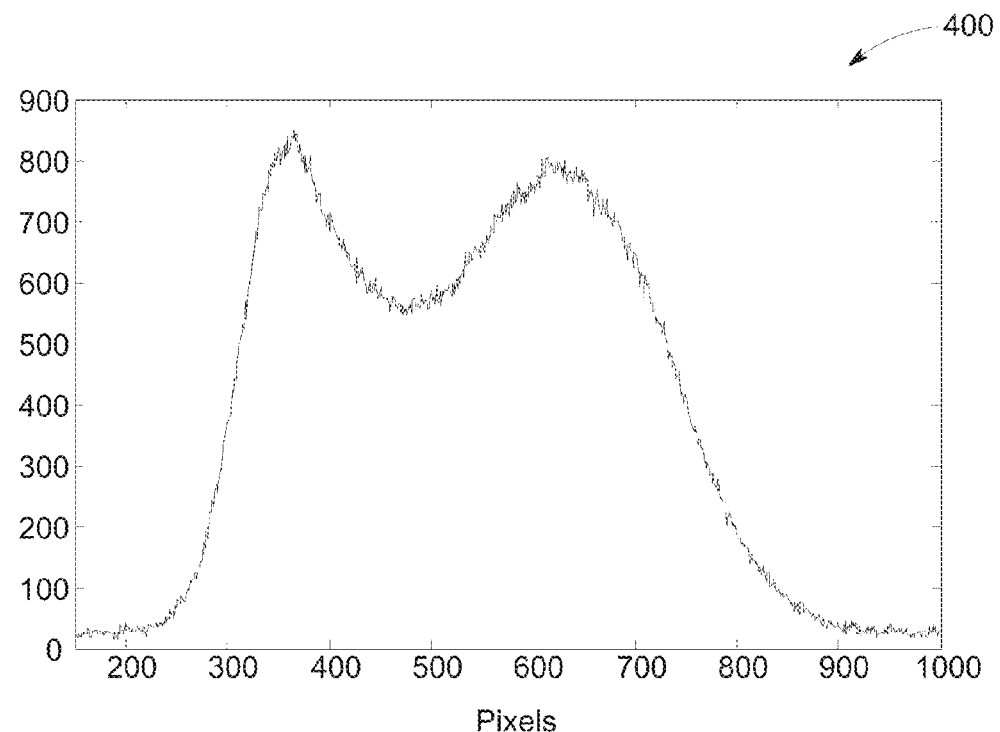
FIG. 4 is a graphical representation depicting a source spectrum measurements obtained using the spectrometer depicted in FIG. 2.

Particularly, FIG. 3 illustrates a graphical representation 300 depicting a source spectrum measurements obtained using a conventional spectrometer. Further, FIG. 4 illustrates a graphical representation 400 depicting a source spectrum measurements obtained using the spectrometer depicted in FIG. 2. As evident from the depictions of FIGS. 3-4, unlike conventional spectrometers, the spectrometer 200 of FIG. 2 is able to capture a larger source spectrum, thereby aiding in achieving an optimal or a desired axial resolution in the resulting cross-sectional OCT images. As used herein, the term "axial resolution" is used to refer to an ability of the OCT system 112 and/or the system 100 to distinguish between two structures that lie along an axis parallel to the incident light beams as separate and distinct. A superior axial resolution allows for optimal imaging of the structures of interest in the sample 102, in turn, aiding in determining desired diagnostic parameters about the sample 102 with greater accuracy.

With returning reference to FIG. 1, the axial resolution of the OCT system 112 depends upon a central wavelength and a bandwidth of the light source 114. Accordingly, the axial resolution may be represented, for example, using equation (1).

$$\Delta z = \frac{2\ln 2}{\pi} \frac{\lambda^2}{\Delta \lambda} \quad (1)$$

where $\Delta z$ corresponds to the axial resolution of the OCT system 112 in air, $\lambda$ corresponds to the central wavelength of the light source 114, and $\Delta\lambda$ corresponds to the bandwidth of the light source 114.

Thus, for a light source having a central wavelength of about 845 nanometers (nm) and a bandwidth of about 45 nm, the axial resolution in air will be 7 µm.

Similarly, an axial resolution of the cross-sectional OCT images in a target tissue $\Delta z_T$ may be determined by modifying equation (1), for example, as indicated by equation (2).

$$\Delta z_T = \frac{\Delta z}{n} \quad (2)$$

where n is the refractive index of the target tissue.

Figure 5:
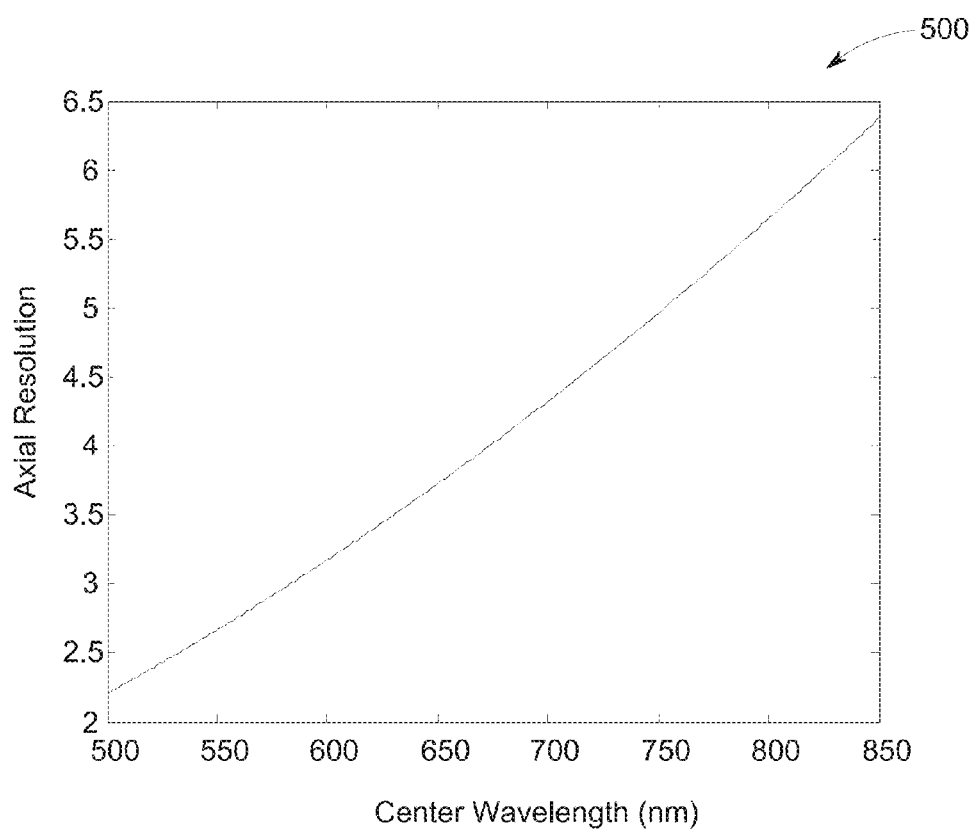
FIG. 5 is a graphical representation that depicts an exemplary change in axial resolution of an optical coherence tomography (OCT) system of FIG. 1 for different central wavelengths of an associated light source, in accordance with aspects of the present specification.
Figure 6:
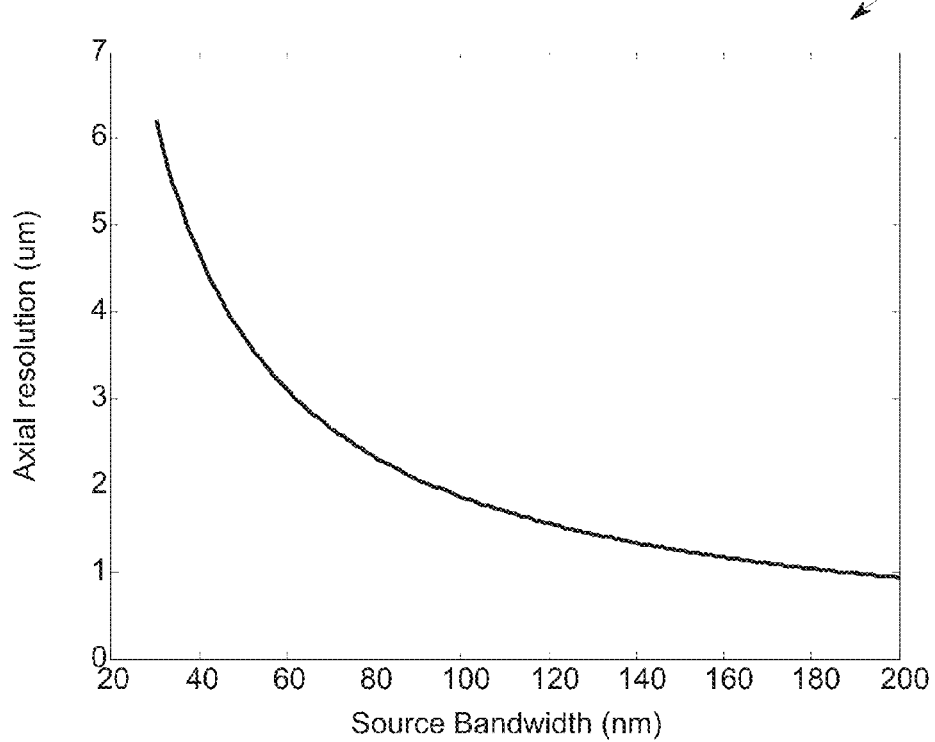
FIG. 6 is a graphical representation that depicts an exemplary change in axial resolution of the OCT system of FIG. 1 for different bandwidths of an associated light source, in accordance with aspects of the present specification.

Assuming that the target tissue has a refractive index of 1.4, the axial resolution $\Delta z_T$ in the target tissue will be 5 µm. The OCT system 112, thus, provides better axial resolution when imaging within tissues as compared to imaging in air. In certain embodiments, the axial resolution of the OCT system 112 may be further enhanced by employing a shorter wavelength and/or the light source 114 having a broader bandwidth. FIGS. 5 and 6 illustrate measured changes in the axial resolution of the OCT system 112 for different central wavelengths and bandwidths.

Specifically, FIG. 5 illustrates a graphical representation 500 that depicts an exemplary change in axial resolution of the OCT system 112 of FIG. 1 for different central wavelengths of the light source 114. Furthermore, FIG. 6 illustrates a graphical representation 600 that depicts an exemplary change in axial resolution of the OCT system 112 of FIG. 1 for different bandwidths of the light source 114 employed for imaging the sample 102. As evident from the depictions of FIGS. 5-6, axial resolution increases with increase in bandwidth and decrease in center wavelength of the light source 114.

However, a higher axial resolution may result in a smaller depth scanning range of the OCT system 112. As used herein, the term "depth scanning range" is used to refer to a determined range of depth up to which the OCT system 112 may obtain measurements during a single axial scan. Generally, for the spectral domain OCT system 112, the depth scan range may be represented, for example, using equation (3).

$$l\max = \frac{\Delta z}{2} * \frac{N}{2} = \frac{\ln 2}{2\pi} \frac{\lambda^2}{\Delta \lambda} N \quad (3)$$

where $\Delta z$ corresponds to the axial resolution in air and N is the number of effective pixels in the detector 144. An increase in number of effective pixels and/or sensitivity of the detector 144, thus, improves the depth scanning range.

In accordance with aspects of the present specification, different trade-offs between values for the desired axial resolution and the depth scanning range are employed for use in different imaging applications. An exemplary imaging scan entailing an OCT scan trace of a 1 mm glass slide having a refractive index 1.52 is depicted in FIG. 7.

Figure 7:
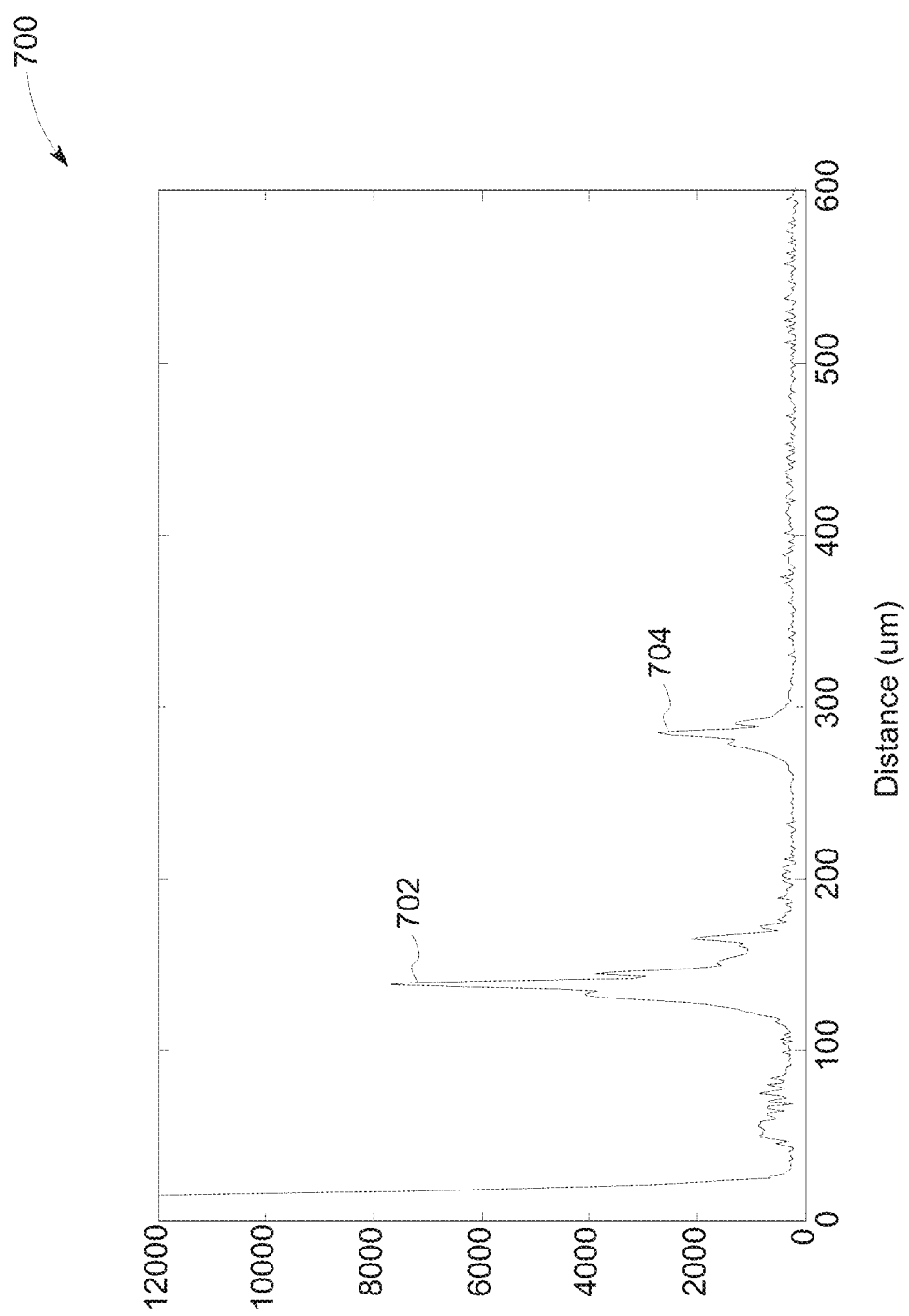
FIG. 7 is a graphical representation indicative of a scan trace obtained by the OCT system of FIG. 1 when imaging a sample, in accordance with aspects of the present specification.

Particularly, FIG. 7 illustrates a graphical representation 700 indicative of a scan trace obtained by the OCT system 112 of FIG. 1 when imaging the sample 102 (see FIG. 1). In one exemplary implementation, the sample 102 is positioned between the coverslip 106 having a thickness of about 0.17 mm and the slide interface 108 having a thickness of about 1 mm Typically, if an overall thickness of the slide 109 (see FIG. 1) is more than a scanning range of the OCT system 112 (about 1.1 mm in glass), the scan trace may not show all the peaks corresponding to the sample 102 and/or the slide 109. Accordingly, the slide 109 may need to be translated axially to capture peaks from other surfaces of the slide 109. In the graphical representation 700, the scan trace includes peaks 702 and 704 that are representative of an axial location of the coverslip 106 and the sample 102, respectively.

However, even when the light incident on the slide 109 moves off the sample 102, top and bottom surfaces of the sample 102 may be visible in the resulting OCT scan trace. Specifically, the top and bottom surfaces of the sample 102 may be visible in the scan trace due to a difference in an index of refraction profile corresponding to the coverslip 106, the slide interface 108, and/or any air bubbles existing between the coverslip 106, the slide interface 108. Accordingly, different OCT scan traces may be evaluated to characterize a shape and profile of the light incident on and off tissue. In particular, peak of the OCT scan trace may be filtered to determine when the microscope 104 is focused on the sample 102 or off the sample 102 for determining the optimal focal position.

With returning reference to FIG. 1, the OCT system 112 may be used to determine the optimal focal position. Specifically, an interference pattern generated by the OCT system 112 may be recorded and/or processed to generate one or more cross-sectional images of the sample 102 having a desired axial resolution. The cross sectional images, in turn, may provide information regarding spatial dimensions and/or location of structures of interest within the sample 102 with the desired resolution to aid in determining exact axial location of a desired region in the sample 102. The axial information, thus determined from the cross-sectional images, may be used to automatically position the sample 102 at an optimal focal position for imaging the desired region.

Particularly, in one embodiment, the system 100 may include a computing device 142 configured to process the cross-sectional OCT images of the sample 102, for example via pattern recognition, to determine a corresponding axial location of the desired region in the sample 102. In one embodiment, the computing device 142 may be operatively coupled to the OCT system 112 and/or the microscope 104 over one or more wired and/or wireless links 116, for example, for receiving the cross-sectional OCT images. Further, the computing device 142 may process the cross-sectional OCT images using suitable techniques to determine a relative axial location of the sample 102. To that end, the computing device 142 may include a one or more graphical processing units, digital signal processors, microcomputers, microcontrollers, application-specific processors, Application Specific Integrated Circuits (ASICs), Field Programmable Gate Arrays (FPGAs), Programmable Logic Arrays (PLAs), and/or other suitable processing devices.

As previously noted, the axial location may be used for reconfiguring and/or repositioning the microscope 104 at a determined optimal focal position suitable for generating images of the sample 102 having a desired resolution. Generally, the optimal focal position or plane for imaging the sample 102 may be determined using a specification sheet for the objective lens 128. Particularly, the specification sheet may list optimal focal distance, for example, corresponding to different positions of an outermost optical surface of the objective lens 128. Accordingly, in one embodiment, the OCT system 112 may be configured to scan the slide 109 to identify the outermost optical surface and a corresponding location of the sample 102. Subsequently, the sample 102 and/or the objective lens 128 may be repositioned to an optimal focal distance listed in the specification sheet. In certain embodiments, an initial slide may further undergo an image-based adjustment to be positioned at the optimal focal position. However, subsequent slides may be positioned at the optical focal position that is initially determined for optimal imaging of the sample 102.

Accordingly, in certain embodiments, the computing device 142 may communicate the relative axial location of the sample 102 and/or the optical focal position to a positioning subsystem 144. In accordance with certain aspects of the present specification, the positioning subsystem 144 may be operatively coupled to the microscope stage 110 to automatically move the stage 110 and/or the sample 102 to the optimal focal position. In one embodiment, the microscope stage 110 may be a motorized stage actuated via one or more control signals received from the computing device 142 and/or processing circuitry (not shown) in the positioning subsystem 144. Additionally, the positioning subsystem 144, for example, may include an actuator, one or more shims, roller bearings, or other suitable positioning elements that may allow for movement of the slide 109, the stage 110, and/or the sample 102. Particularly, the positioning subsystem 144 may be configured to move the slide 109, the stage 110, and/or the sample 102 a determined distance along one or more three-dimensional (3D) axes to automatically position a target region in the sample 102 at the optimal focal spot location. A method for accurately determining the distance by which the slide 109, the stage 110, and/or the sample 102 need to be moved into the optimal position may be described in greater detail with reference to FIG. 8.

Figure 8:
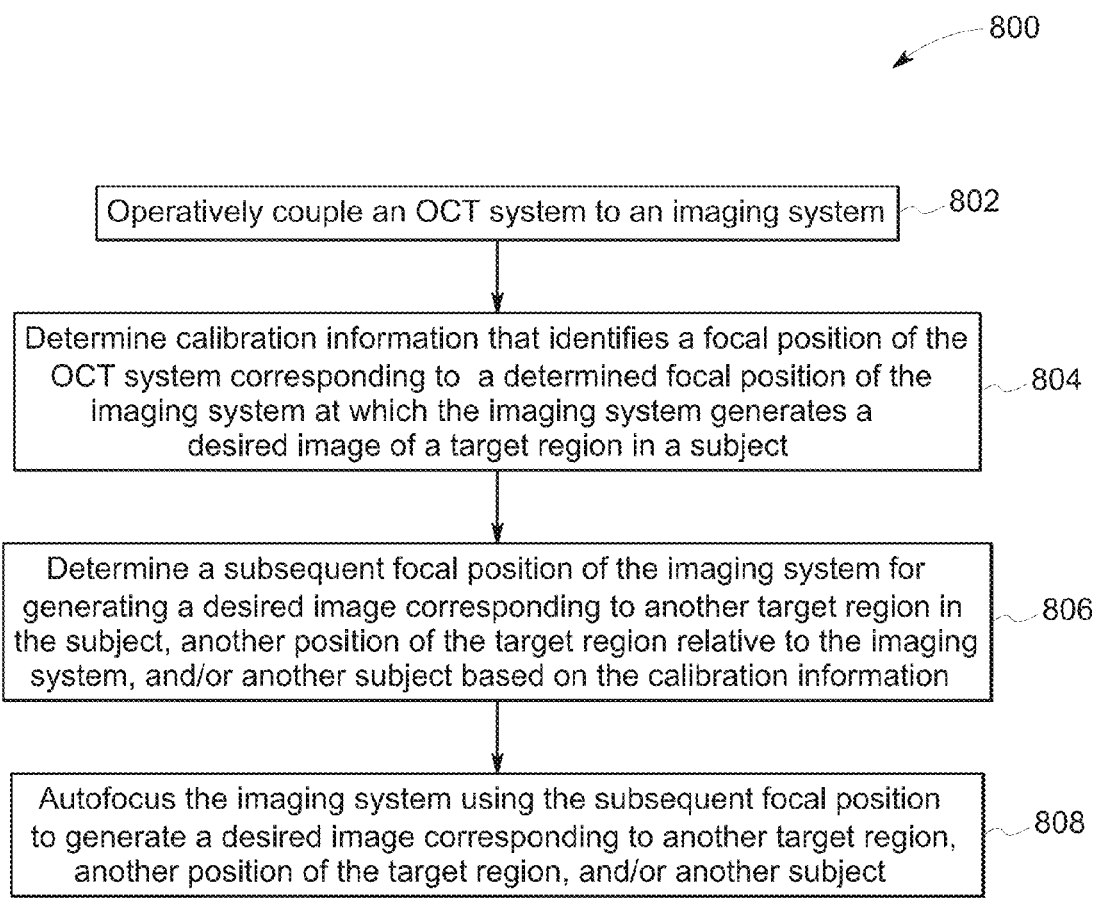
FIG. 8 is a flow chart depicting exemplary method for an OCT-assisted autofocusing of an imaging system, in accordance with aspects of the present specification.

FIG. 8 illustrates a flow chart 800 depicting an exemplary method for an OCT-assisted autofocusing of an imaging system. In the present specification, embodiments of the exemplary method may be described in a general context of computer executable instructions on a computing system or a processor. Generally, computer executable instructions may include routines, programs, objects, components, data structures, procedures, modules, functions, and the like that perform particular functions or implement particular abstract image data types.

Additionally, embodiments of the exemplary method may also be practiced in a distributed computing environment where optimization functions are performed by remote processing devices that are linked through a wired and/or wireless communication network. In the distributed computing environment, the computer executable instructions may be located in both local and remote computer storage media, including memory storage devices.

Further, in FIG. 3, the exemplary method is illustrated as a collection of blocks in a logical flow chart, which represents operations that may be implemented in hardware, software, or combinations thereof. The various operations are depicted in the blocks to illustrate the functions that may be performed, for example, during the steps of determining calibration information and/or autofocusing the imaging system in the exemplary method. In the context of software, the blocks represent computer instructions that, when executed by one or more processing subsystems, perform the recited operations.

The order in which the exemplary method is described is not intended to be construed as a limitation, and any number of the described blocks may be combined in any order to implement the exemplary method disclosed herein, or an equivalent alternative method. Additionally, certain blocks may be deleted from the exemplary method or augmented by additional blocks with added functionality without departing from the spirit and scope of the subject matter described herein. For discussion purposes, the exemplary method will be described with reference to the elements of FIGS. 1-2.

Embodiments of the present method advantageously employ superior axial resolution provided by OCT images to accurately determine a distance by which a slide such as slide 109 and/or stage 110 of FIG. 1 need to be moved. Specifically, the method determines the distance by which the slide 109 and/or stage 110 need to move to be automatically positioned for optimal imaging of the sample 102 (see FIG. 1) by the microscope 104.

The method begins at step 802, where an OCT system such as the OCT system 112 of FIG. 1 may be operatively coupled to an imaging system such as the microscope 104 of FIG. 1. By way of example, the OCT system may be coupled to the imaging system via one or more electrical, electronic, and/or communications links such as a local area network and/or the Internet.

In one embodiment, the imaging system is configured to generate a desired image of a subject such as a biological tissues and/or a non-biological object of interest. As used herein, the term "desired image" may be used to refer to an image that satisfies at least one selected quality metric such as a desired intensity, noise level and/or SNR that may be predefined and/or may be input by a user during imaging. According to aspects of the present specification, one or more cross-sectional images of the subject generated by the OCT system may be used to identify axial location information. The axial location information, in turn, may be used to identify an optimal focal position of the imaging system that allows for generation of the desired image.

Accordingly, at step 804, calibration information that identifies a focal position of the OCT system corresponding to a determined focal position of the imaging system at which the imaging system generates a desired image of a target region in a subject may be determined Determination of the calibration information is described in greater detail with reference to FIG. 9.

Figure 9:
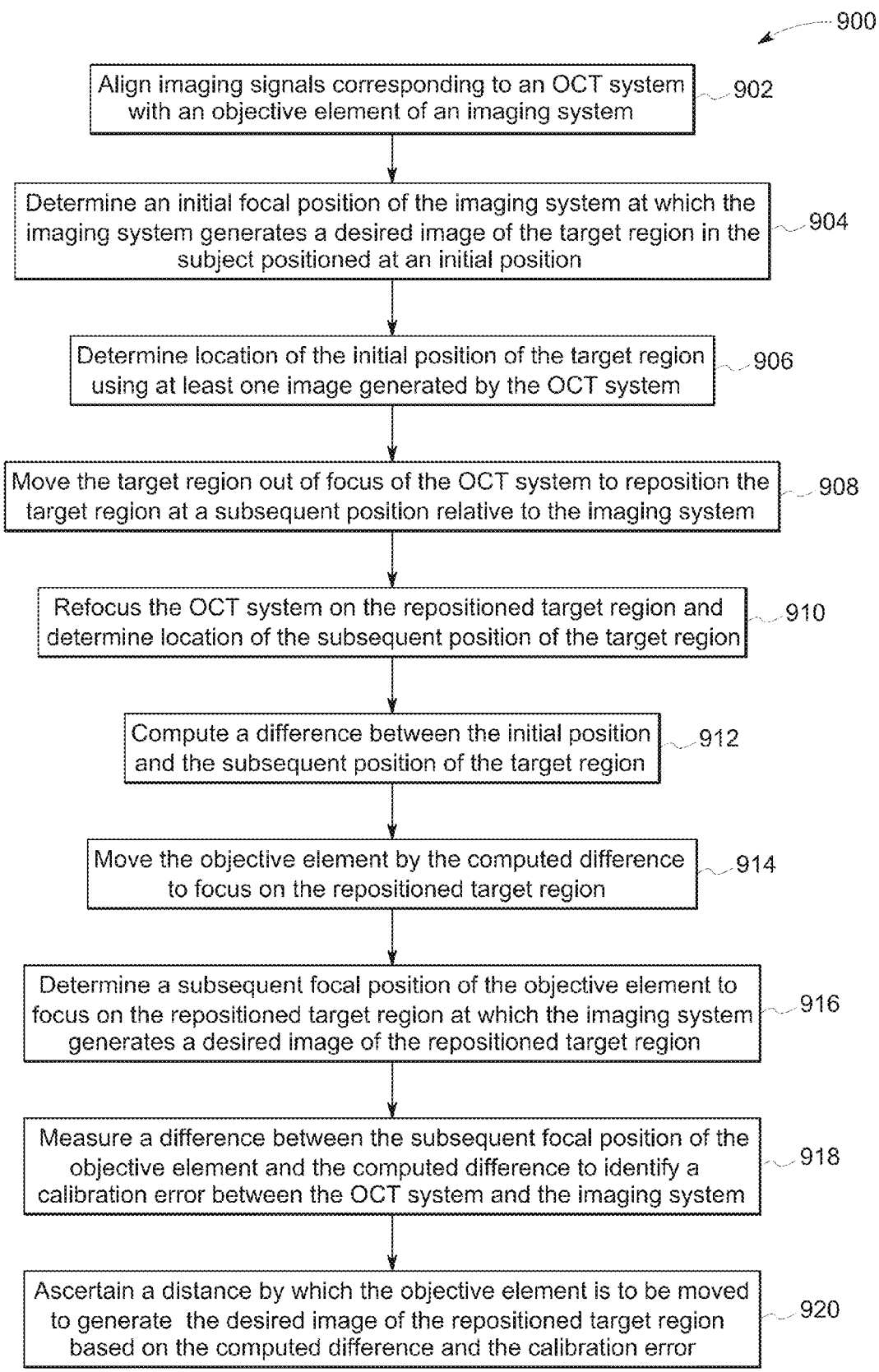
FIG. 9 is a flow chart depicting an exemplary method for determining calibration information that aligns the OCT system with the imaging system, in accordance with aspects of the present specification.

Particularly, FIG. 9 illustrates a flow chart 900 that depicts an exemplary method for determining calibration information that aligns a focal position of the OCT system with a corresponding focal position of the imaging system for imaging a target region in the subject. At step 902, imaging signals corresponding to the OCT system are aligned with an objective element of the imaging system. Particularly, the OCT system and the imaging system are aligned such that the OCT system is configured to probe the same target region that is being imaged by the imaging system. Accordingly, in one example, the sample channel 122 (see FIG. 1)

of the OCT system may be adjusted in an X and/or Y direction to be aligned with an objective element of the imaging system.

Further, at step 904, an initial focal position of the imaging system at which the imaging system generates a desired image of the target region in the subject positioned at an initial position may be determined Specifically, the objective lens 128 and/or the slide 109 may be adjusted to identify the best or a desired focal position for imaging the target region. Moreover, at step 906, location of the initial position of the target region may be determined using at least one image generated by the OCT system. To that end, in one example, an image-based focusing method may be used to determine the best or a desired focal position for generating a desired cross-sectional image of the target region. The cross-sectional image, in turn, may be used to determine an initial position or axial location of the subject such as the sample 102 (see FIG. 1) relative to a reference point such as the objective element of the imaging system.

With returning reference to FIG. 9, at step 908, the target region is moved out of focus of the OCT system so as to reposition the target region at a subsequent position relative to the imaging system. Particularly, the target region may be repositioned at a pre-programmed and/or user-defined distance relative to the objective element of the imaging system. In one embodiment, the target region may be moved via use of an actuator, one or more shims, roller bearings, and/or other suitable positioning elements such as described with reference to the positioning subsystem 144 of FIG. 1 that are operatively coupled to the OCT system and/or the imaging system.

Further, at step 910, the OCT system is refocused on the repositioned target region, and subsequently, location of the subsequent position of the target region is measured via use of the OCT system. In one embodiment, the initial and subsequent positions of the target region are measured by processing corresponding cross-sectional OCT images of the target region. Particularly, in one embodiment, the computing device 142 and/or the positioning subsystem 144 of FIG. 1 may be configured to determine the initial and the subsequent location of the target region by processing the cross-sectional images of the target region that are acquired at the initial and subsequent positions, respectively.

Figure 10:
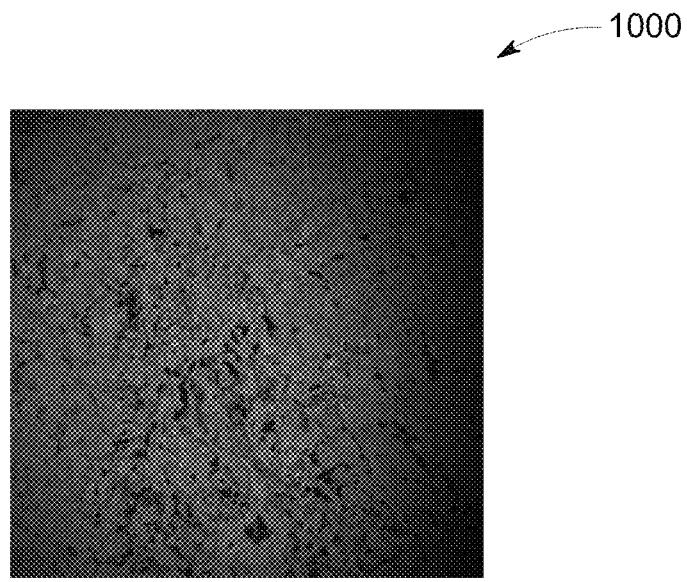
FIG. 10 is a desired OCT image that visualizes the target region in the subject that is positioned at an initial position, in accordance with aspects of the present specification.
Figure 11:
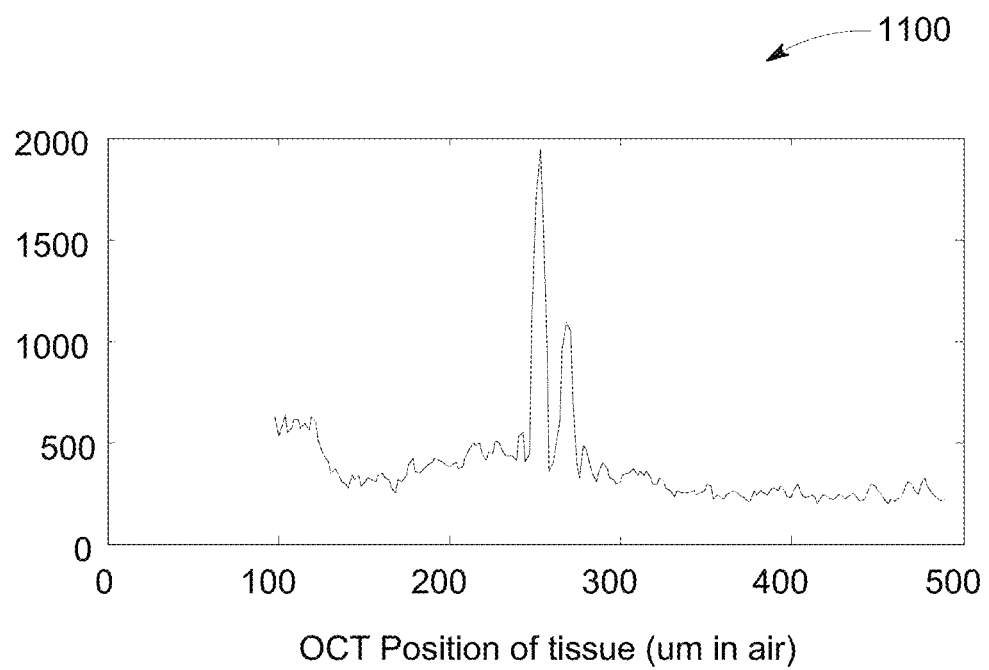
FIG. 11 is a graphical representation depicting an exemplary OCT trace corresponding to the initial position of the target region, in accordance with aspects of the present specification.

FIG. 10 illustrates an example of a desired image 1000 corresponding to a cross-sectional OCT image that visualizes the target region in the subject that is positioned at an initial position. As depicted in the image 1000, the initially focused OCT image provides desired visualization of one or more desired features in the target region. Additionally, FIG. 11 illustrates an exemplary graphical representation 1100 depicting an exemplary OCT trace corresponding to the initial position of the target region. As previously noted, the cross-sectional images such as the image 1000 of FIG. 10 may be evaluated for determining an initial axial position of the target region. Specifically, in the embodiment depicted in FIG. 11, the initial axial position of the target region is determined via use of a cross-sectional OCT image to be about 261.4 um.

Figure 12:
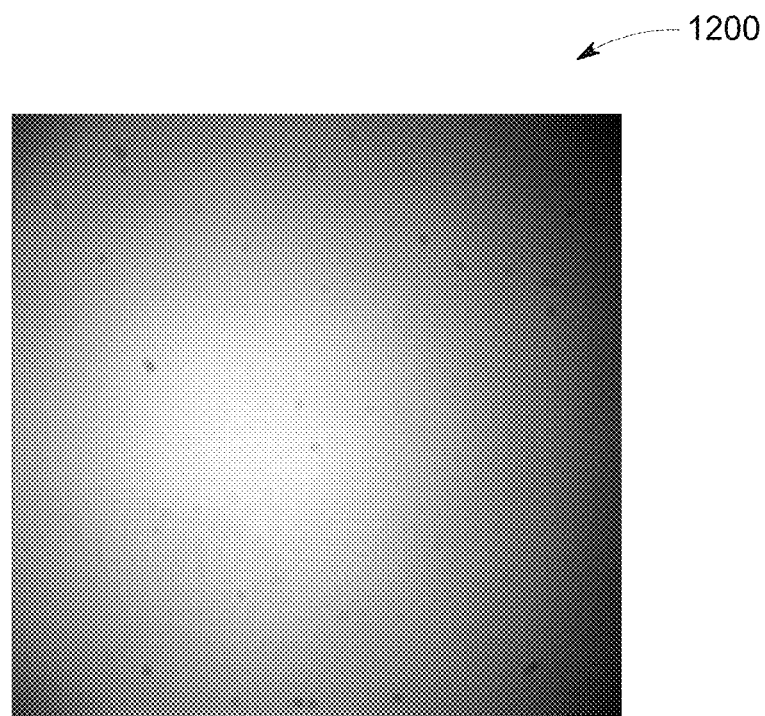
FIG. 12 is an example of an unfocused image generated by the OCT system when a target region is moved out of focus to a subsequent position, in accordance with aspects of the present specification.
Figure 13:
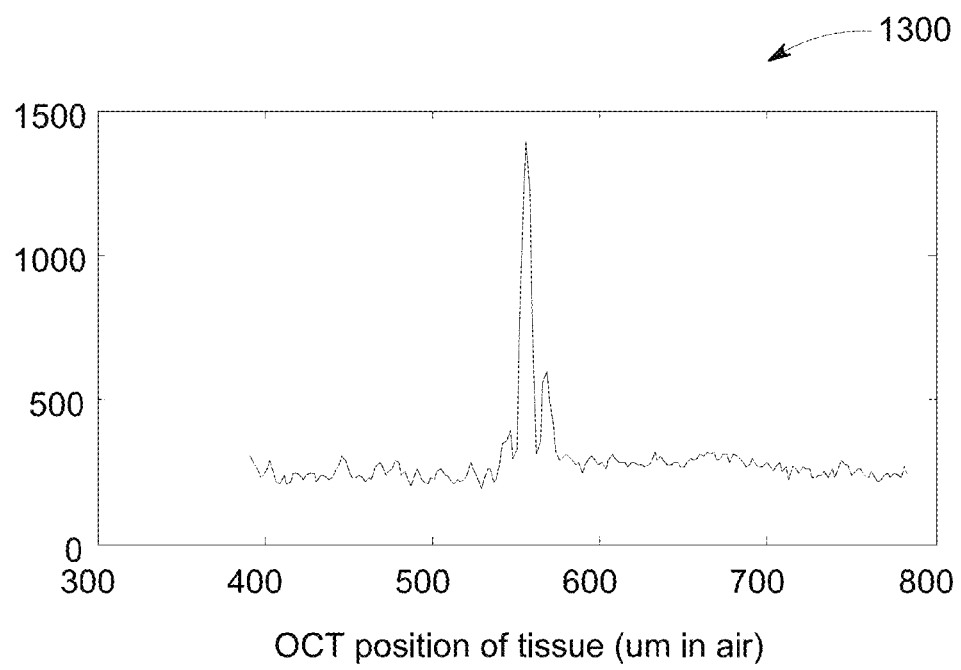
FIG. 13 is a an exemplary graphical representation depicting an exemplary OCT trace obtained at the subsequent position of the target region, in accordance with aspects of the present specification.

Further, FIG. 12 illustrates an example of an unfocused image 1200 generated by the OCT system when the target region is moved out of focus to s subsequent position. As depicted in the image 1200, the unfocused OCT image 1200 fails to provide any distinctive features corresponding to the target region. However, FIG. 13 illustrates an exemplary graphical representation 1300 depicting an exemplary OCT trace obtained at the subsequent position of the target region. Particularly, in the embodiment depicted in FIG. 13, the subsequent axial position of the target region is determined by the OCT system to be about 556.4 um.

With returning reference to FIG. 9, at step 912, a difference between the initial position and the subsequent position of the target region is computed. With reference to the examples depicted in FIGS. 11 and 13, the computed difference may correspond to about 295 μm. In certain embodiments, the computed difference may be representative of an unknown distance by which the target region was moved at step 908.

Accordingly, at step 914, the objective element of the imaging system is moved by the computed difference to focus on the repositioned target region. Moving the objective element by the computed difference compensates for the movement of the target region in step 908. Alternatively, the objective element may be moved to a predetermined optimal or clinically specified position of the objective element corresponding to the subsequent position of the target region determined via use of the OCT system.

However, moving the objective element by the computed difference may not be sufficient for generating a desired image of the target region at the subsequent position due to a calibration error between the imaging system and the OCT system. Thus, at step 916, a subsequent focal position of the objective element to focus on the repositioned target region may be determined at which the imaging system generates a desired image of the repositioned target region.

Further, at step 918, a difference between the subsequent focal position of the objective element and the computed difference is measured to identify a calibration error between the OCT system and the imaging system. Certain examples of the calibration error measured at two exemplary positions of the target region when using a 20×0.45 NA objective element having a depth of Field (DOF) of 5.14 μm are depicted in Table 1.

TABLE 1

| Position of Target region | OCT-derived Subsequent Position | Subsequent Focal Position of Objective Element | Calibration Error |
| --- | --- | --- | --- |
| Initial | 6386.42 μm | 6387.92 μm | 1.5 μm |
| Subsequent | 6358.75 μm | 6356.84 μm | −1.91 μm |

As depicted in Table 1, the OCT autofocusing successfully refocused on the sample after its movement, with high speed and with less than 2 μm in difference compared to image based focusing. This is comparable to the depth of field (DOF) of a 20×0.75 NA objective at 520 nm (1.85 μm). However, OCT-derived position measurements may show variability due to fixed pattern noise such as system vibration, fixed phase shift noise, and fixed electronics noise. Accordingly, in certain embodiments, a final calibration error may be determined by averaging OCT traces for a plurality of positions (for example, about 100 positions) of the target region.

At step 920, a calibration distance by which the objective element is to be moved to generate the desired image of the repositioned target region is ascertained based on the computed difference and the calibration error. The calibration distance information may be fed back to the imaging system to autofocus the objective element for optimal imaging the target region at one or more other locations without repeated repositioning of the objective element and/or corresponding image acquisition and processing.

Accordingly, with returning reference to FIG. 8, at step 806, a subsequent focal position of the imaging system may be determined for generating a desired image corresponding to another target region in the subject, another position of the target region relative to the imaging system, and/or another subject based on the calibration information. Specifically, in one embodiment, the OCT system may be configured to image the target region located in another location, another target region on the slide, and/or a sample from another subject to determine the axial location of the repositioned target region. The computing device and/or the positioning system may then use the calibration information to compensate for calibration error in a determined difference between the axial location and a previous location. The difference, thus determined, may be communicated to the positioning subsystem to identify the subsequent focal position of the imaging system for optimally imaging the repositioned target region.

Particularly, at step 808, the imaging system is autofocused using the subsequent focal position to generate a desired image corresponding to another target region, another position of the target region, and/or another subject. Thus, use of the calibration information and the axial location information determined by the OCT system allows for rapidly autofocusing of the imaging system on to one or more subsequent positions to which the slide may be repositioned. Specifically, use of the OCT-derived location information provides accurate guidance for rapid autofocusing of the objective element without moving the objective element or the slide 109. Additionally, use of the OCT-derived location information provides a low-cost autofocusing technique that eliminates repeated acquisition and processing of a series of defocused images to identify optimal or desired focus for successive imaging scan of one or more target regions.

Figure 14:
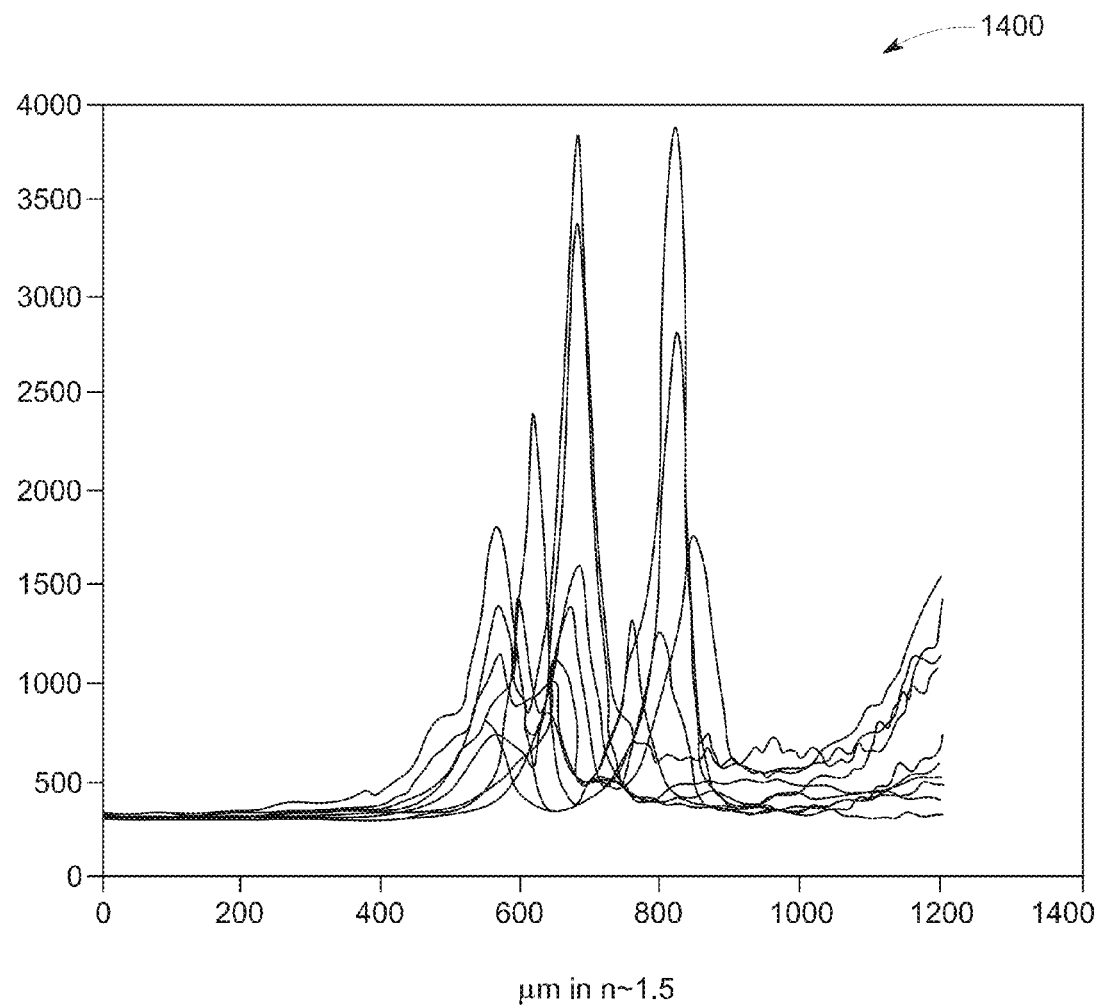
FIG. 14 is an exemplary graphical representation representative of laser trace measurements obtained by imaging a target region of a subject, in accordance with aspects of the present specification.
Figure 15:
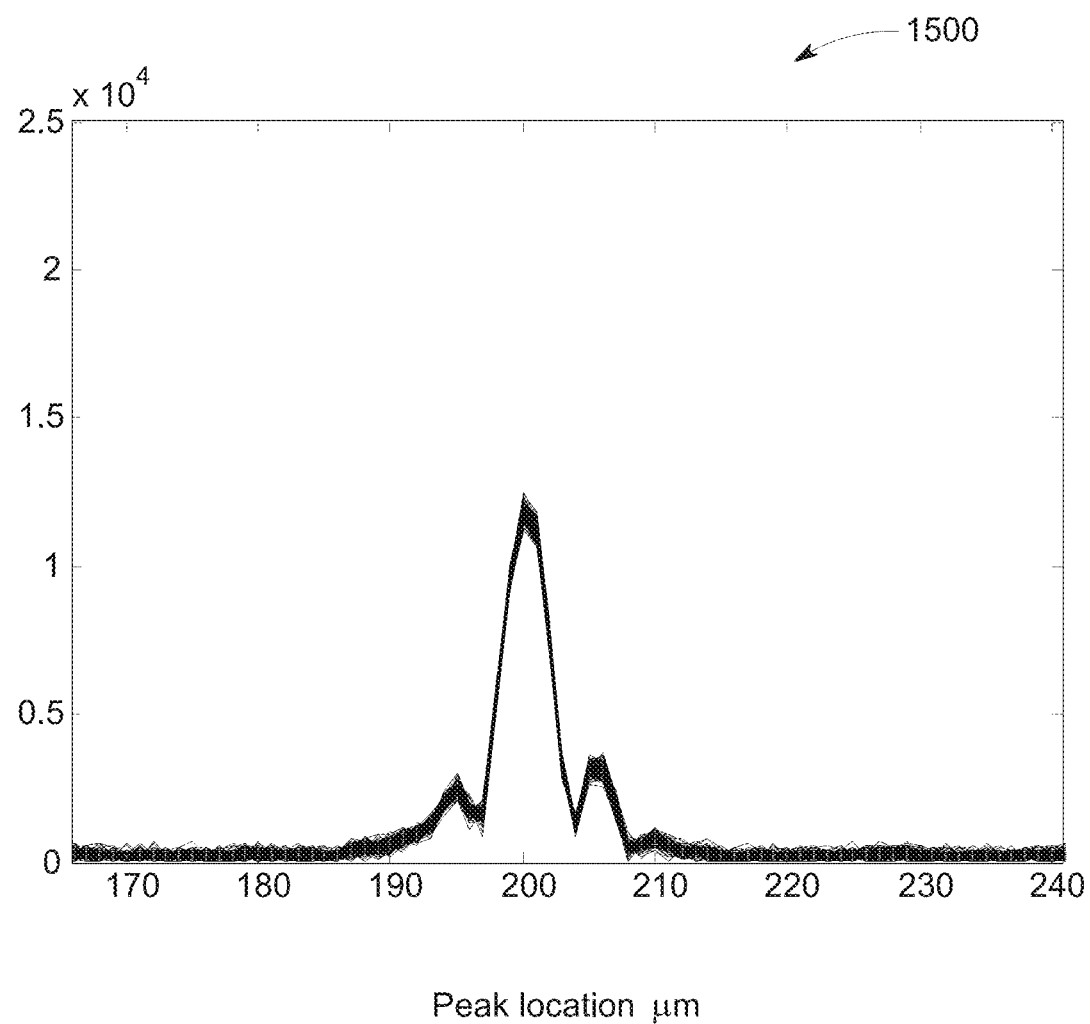
FIG. 15 is an exemplary graphical representation representative of OCT trace measurements obtained by imaging the target region, in accordance with aspects of the present specification.

FIGS. 14 and 15 depict a comparison of autofocusing performance when using a conventional laser-based focusing method and an embodiment of the method described with reference to FIGS. 8-13, respectively. Particularly, FIG. 14 illustrates an exemplary graphical representation 1400 representative of laser trace measurements obtained by imaging a target region of a subject such as biological tissues. As depicted in FIG. 14, the laser traces includes weak signals that are neither repeatable nor provide consistent and/or accurate locations of the sample or target region being evaluated. Moreover, each laser trace takes about 1-2 seconds to complete, thereby delaying the diagnostic imaging procedure significantly.

Conversely, FIG. 15 illustrates an exemplary graphical representation 1500 representative of OCT trace measurements obtained by imaging the target region. Unlike the weak laser trace signals depicted in FIG. 14, the OCT trace measurements provide consistent and/or accurate locations of the sample or target region being evaluated. In an exemplary implementation, a repeatability of OCT auto focusing was found to be better than the laser trace autofocusing in a preliminary comparison. Furthermore, the OCT system is capable of collecting more than 100 samples of OCT trace in about 3 milliseconds, thereby providing a tracing speed that is about 500 times faster than the laser trace technique. High speed operation of the OCT system allows for averaging and/or implementation of other processing steps that further improves an accuracy of determining the location of the target region without repeated repositioning of the sample or the objective element. Use of the OCT-derived information, thus, provides significant improvement in accuracy as well as total time spent during diagnostic imaging. In one example, the overall focus time is shortened by 88% with selected parameter settings for the OCT system.

However, as previously noted, use of the OCT system entails a trade-off between axial resolution and depth scanning range. Generally, higher the axial resolution, smaller will be the depth scanning range. Accordingly, performance parameters of the auto focusing system such as the system 100 may be designed differently for different applications. One implementation, for example, may entail use of an OCT system having a depth scanning range of about 5-10 millimeter (mm) and an axial resolution of about 20 µm. Such a large depth scanning range may allow the autofocusing system to locate positon of the target region and the objective element simultaneously.

As a working distance of the objective element may be known, the auto focusing system may be used to achieve the initial focus after installing the slide into the microscope, thereby preventing a need for manual and time consuming focal adjustments corresponding to the imaging system such as a microscope. Although such an OCT system may not localize depth of tissue (several microns in thickness) consistently, the OCT system may still generate a broad peak signal corresponding to the target region, thereby brining the target region closer to a desired focus. Moreover, with the present implementation, a three-point image based autofocusing for about 1-2 seconds may be used to obtain the desired focus for high numerical aperture (NA) objective elements, whereas a single OCT trace may suffice for low NA (about 0.1-0.45) objective elements.

In another implementation, however, an OCT system having a small depth rage of about 1-2 mm and an axial resolution of about 3-5 µm may be used. In such an implementation, the high axial resolution allows the autofocusing system to locate the target region accurately, thereby eliminating a need for any image based focusing and allowing for faster imaging. By way of example, when imaging a target region having a size of about 15 mm×15 mm using a 20×0.75 NA objective and 4 spectral channels, a focusing time may was shortened from about 11.5 minutes to about 1.7 minutes. Use of the present implementation, thus reduced a total imaging time from about 27.6 minutes to about 17.8 minutes. In certain scenarios, the autofocusing may also be supplemented with other gross focusing methods such as laser or image based focusing to correct for large focus offsets.

In a presently contemplated embodiment, an embodiment of the autofocusing system having high axial resolution and lower depth scanning range may be used in the General Electric Company's Omnyx™ systems that provide integrated digital pathology solution. Specifically, the autofocusing system having high axial resolution and lower depth scanning range may be used in a closed loop in the Omnyx™ systems to always keep the slide in focus with high speed and accuracy.

Figure 16:
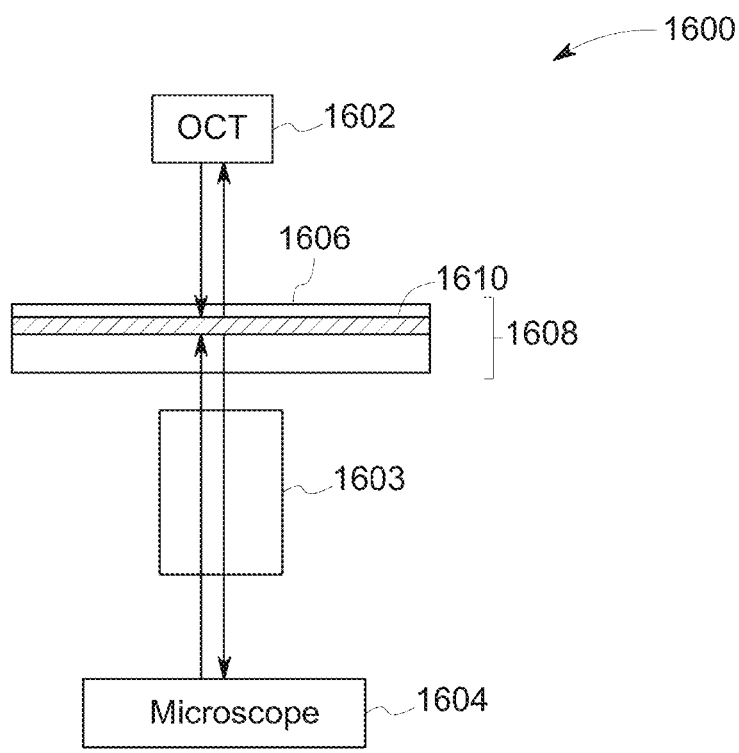
FIGS. 16-18 are block diagrams of exemplary configurations of an autofocusing system, in accordance with aspects of the present specification.
Figure 17:
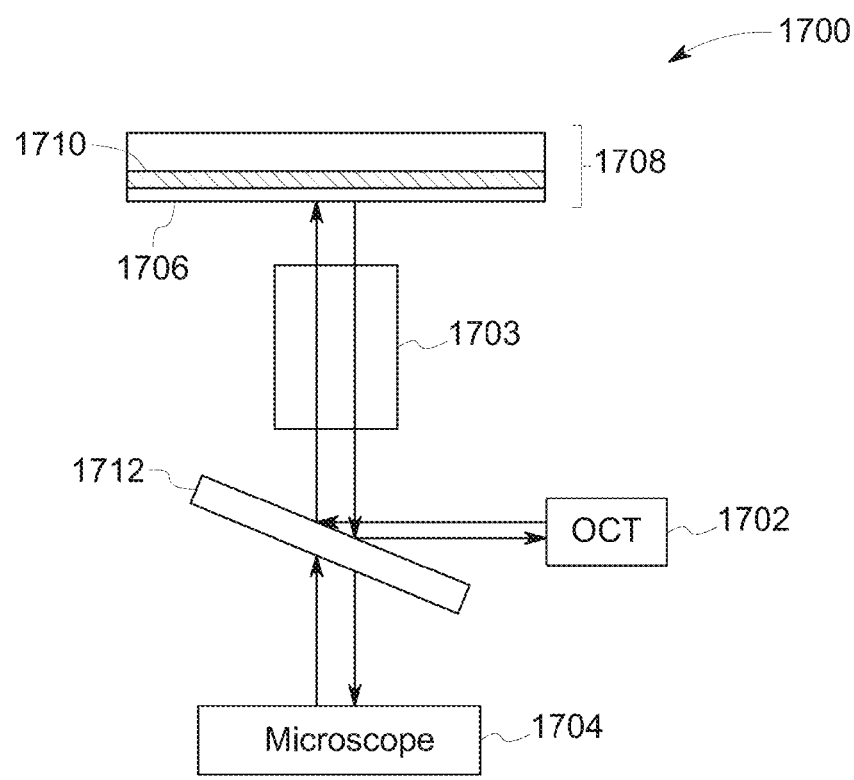
Figure 18:
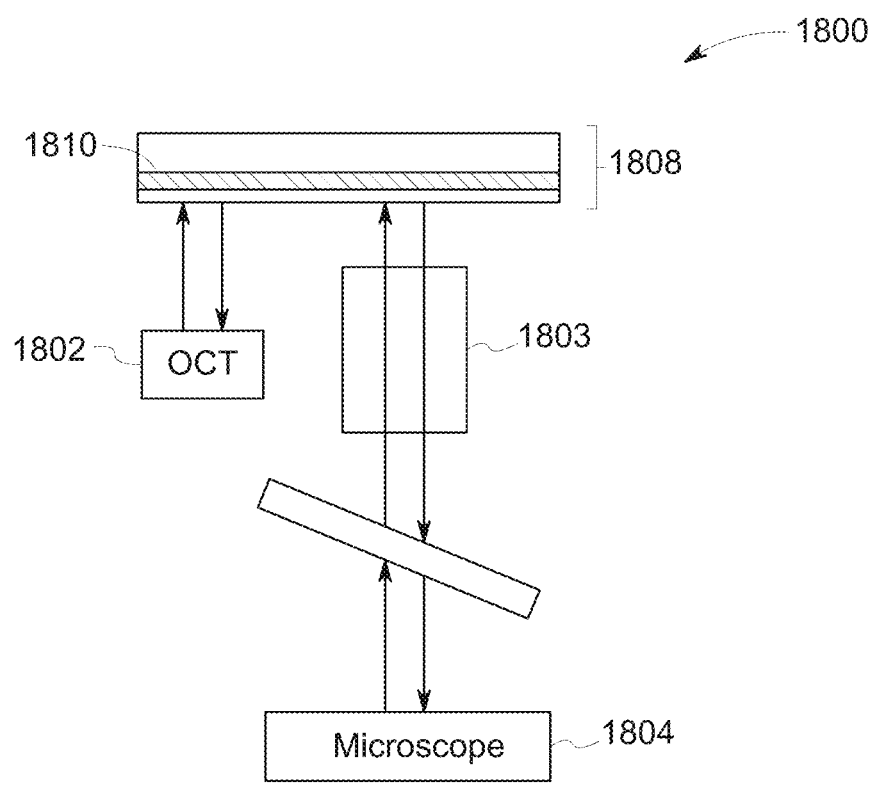

Certain configurations of the OCT system for use in the autofocusing system 100 of FIG. 1 are depicted in FIGS. 16-18. Particularly, FIG. 16 illustrates a block diagram of an exemplary configuration of an autofocusing system 1600, such as the system 100 of FIG. 1, where an OCT system 1602 is positioned above an objective lens 1603 of a microscope 1604. Alternatively, the OCT system 1602 and the microscope 1604 are positioned on opposite sides of a coverslip 1606 of a slide 1608 carrying a sample 1610 to be imaged. Particularly, the configuration depicted in FIG. 16 allows the OCT system 1602 and/or the microscope 1604 to operate independently of each other. In order to provide robust autofocusing performance in different imaging scenarios, the autofocusing system 1600 may have a relatively large depth scanning range from the OCT system 1602 to image through the 1 mm slide glass. Furthermore, use of the autofocusing system 1600 may entail additional steps that calibrate a relative position of the objective lens 1603 to the OCT system 1602. Additionally, in certain embodiments, the OCT system 1602 may be aligned with the microscope 1604, for example, using the method described with reference to step 902 of FIG. 9.

Further, FIG. 17 illustrates a block diagram of an exemplary configuration of an autofocusing system 1700, where an OCT system 1702 is positioned in front of an objective lens 1703 of a microscope 1704. Alternatively, the objective lens 1703 is positioned between the OCT system 1702 and a coverslip 1706 of a slide 1708 carrying a sample 1710 to be imaged. Additionally, the autofocusing system 1700 may include a beam splitter 1712 configured to aid in generation of cross-sectional OCT images corresponding to the sample 1710. In the configuration depicted in FIG. 17, the OCT system 1702 is aligned along the microscope 1704. The depicted configuration may be implemented to provide a smaller depth scanning range but a higher axial resolution. As the objective lens 1703 may also function as a focusing lens for OCT beams in the depicted configuration, additional circuitry may be employed to operatively couple the OCT beam to a microscope beam.

Moreover, FIG. 18 illustrates a block diagram of an exemplary configuration of an autofocusing system 1800, where an OCT system 1802 is positioned along an objective lens 1803 of a microscope 1804. Specifically, the OCT system 1802 may be positioned on a same side of a slide 1808 as the microscope 1804 to provide superior axial imaging of a sample 1810 mounted on the slide 1808.

Embodiments of the present systems and methods, thus, provide an ability to directly, repeatably, and/or rapidly measure accurate tissue location within a coverslip and slide interface. Specifically, use of a high speed OCT system significantly improves focusing time by identifying good starting axial location for any image based focusing such as for improving microscope operations. Improvements in the microscope operation to shorten the focusing time, in turn, expediting slide scanning, a biomarker multiplexing processing, and/or integrated digital pathology processes.

Although, embodiments of the present systems and methods are described with reference to an OCT-assisted autofocusing system for a microscope, certain embodiments may also find use in non-medical imaging applications. By way of example, the embodiments described herein may be used in the semiconductor industry for providing super-resolution imaging systems for fast and accurate wafer/reticle inspection. In another example, the embodiments of the present systems and methods may be used for rapid and accurate focusing during in vivo imaging of brain tissues in live animals to minimize corresponding image motion artifacts. Particularly, in certain scenarios, the present systems and methods may provide high speed, high volume, and high axial resolution auto focusing without repeated repositioning of the sample or objective and/or without repeated image acquisition and processing. Use of the embodiments of the present system and method, thus, provide significant improvements in cost, accuracy, and/or procedure time associated with diagnostic imaging applications.

It may be noted that the foregoing examples, demonstrations, and process steps that may be performed by certain components of the present systems, for example by the computing device 142, the positioning subsystem 144 of FIG. 1 may be implemented by suitable code on a processor-based system. To that end, the processor-based system, for example, may include a general-purpose or a special-purpose computer. It may also be noted that different implementations of the present specification may perform some or all of the steps described herein in different orders or substantially concurrently.

Additionally, the functions may be implemented in a variety of programming languages, including but not limited to Ruby, Hypertext Preprocessor (PHP), Perl, Delphi, Python, C, C++, or Java. Such code may be stored or adapted for storage on one or more tangible, machine-readable media, such as on data repository chips, local or remote hard disks, optical disks (that is, CDs or DVDs), solid-state drives, or other media, which may be accessed by the processor-based system to execute the stored code.

Although specific features of embodiments of the present specification may be shown in and/or described with respect to some drawings and not in others, this is for convenience only. It is to be understood that the described features, structures, and/or characteristics may be combined and/or used interchangeably in any suitable manner in the various embodiments, for example, to construct additional assemblies and methods for use in enhanced diagnostic imaging.

While only certain features of the present disclosure have been illustrated and described herein, many modifications and changes will occur to those skilled in the art. It is, therefore, to be understood that the appended claims are intended to cover all such modifications and changes as fall within the true spirit of the invention.

The invention claimed is:

1. An autofocusing method, comprising:
providing an imaging system and an optical interferometry system for generating one or more images corresponding to a target region in a subject;
determining calibration information that identifies a focal position of the optical interferometry system corresponding to a determined focal position of the imaging system at which the imaging system generates a desired image of the target region at an initial position, wherein determining calibration information comprises:
aligning the optical interferometry system with an objective element of the imaging system;
determining an initial focal position of the imaging system at which the imaging system generates a desired image of the target region in the subject positioned at an initial position;
determining location of the initial position of the target region using at least one image generated by the optical interferometry system;
moving the target region out of focus of the optical interferometry system to reposition the target region at a subsequent position relative to the imaging system;
refocusing the optical interferometry system on the repositioned target region and determine location of the subsequent position of the target region;
computing a difference between the initial position and the subsequent position of the target region;
moving the objective element by the computed difference to focus on the repositioned target region;
determining a subsequent focal position of the objective element to focus on the repositioned target region at which the imaging system generates a desired image of the repositioned target region;
measuring a difference between the subsequent focal position of the objective element and the computed difference to identify a calibration error between the optical interferometry system and the imaging system; and ascertaining a distance by which the objective element is to be moved to generate the desired image of the repositioned target region based on the computed difference and the calibration error;

determining a subsequent focal position of the imaging system for generating a desired image corresponding to at least one of another target region in the subject and another position of the target region relative to the imaging system based on the calibration information; and autofocusing the imaging system using the subsequent focal position to generate the desired image corresponding to at least one of the another target region in the subject and another position of the target region relative to the imaging system.

2. The method of claim 1, wherein the desired image of the target region corresponds to an image that satisfies at least one selected quality metric.

3. An autofocusing system, comprising:

an imaging system configured to image a target region in a subject;

an optical interferometry system operatively coupled to the imaging system, wherein the optical interferometry system is configured to generate one or more axial images of the target region;

a computing device communicatively coupled to the imaging system and the optical interferometry system, wherein the computing device is configured to:

determine calibration information that identifies an initial focal position of the optical interferometry system corresponding to a determined focal position of the imaging system at which the imaging system generates a desired image of the target region, comprising:

align the optical interferometry system with an objective element of the imaging system;

determine an initial focal position of the imaging system at which the imaging system generates a desired image of the target region in the subject positioned at an initial position;

determine location of the initial position of the target region using at least one image generated by the optical interferometry system;

move the target region out of focus of the optical interferometry system to reposition the target region at a subsequent position relative to the imaging system;

refocus the optical interferometry system on the repositioned target region and determine location of the subsequent position of the target region;

compute a difference between the initial position and the subsequent position of the target region;

move the objective element by the computed difference to focus on the repositioned target region;

determine a subsequent focal position of the objective element to focus on the repositioned target region at which the imaging system generates a desired image of the repositioned target region;

measure a difference between the subsequent focal position of the objective element and the computed difference to identify a calibration error between the optical interferometry system and the imaging system; and ascertain a distance by which the objective element is to be moved to generate the desired image of the repositioned target region based on the computed difference and the calibration error;

determine a subsequent focal position of the imaging system for generating a desired image corresponding to at least one of another target region in the subject and another position of the target region relative to the imaging system based on the calibration information; and autofocus the imaging system using the subsequent focal position to generate the desired image corresponding to at least one of the another target region in the subject and another position of the target region relative to the imaging system; and a positioning subsystem configured to move the target region to the another position relative to the imaging system at which the imaging system is configured to generate a desired image of the repositioned target region using the subsequent focal position, wherein the positioning subsystem is operatively coupled to one or more of the imaging system and the optical interferometry system.

4. The autofocusing system of claim 3, wherein the optical interferometry system comprises an optical coherence tomography system.

5. The autofocusing system of claim 3, wherein the positioning subsystem comprises one or more actuators, shims, roller bearings, positioning elements, or combinations thereof.

6. The autofocusing system of claim 3, wherein the imaging system comprises a microscope, wherein the objective element comprises an objective lens of the microscope and further wherein the optical interferometry system is positioned above the objective lens.

7. The autofocusing system of claim 3, wherein the imaging system comprises a microscope, wherein the objective element comprises an objective lens of the microscope and further wherein the optical interferometry system and the microscope are positioned on opposite sides of a coverslip and a slide interface carrying a sample mounted in between, wherein the sample is imaged by the microscope.

8. The autofocusing system of claim 3, wherein the imaging system comprises a microscope, wherein the objective element comprises an objective lens of the microscope and further wherein the optical interferometry system and the microscope are positioned on the same side of a coverslip and a slide interface carrying a sample mounted in between, wherein the sample is imaged by the microscope.

9. The autofocusing system of claim 3, wherein the imaging system comprises a microscope, wherein the objective element comprises an objective lens of the microscope and further wherein the objective lens is positioned between the optical interferometry system and a coverslip and a slide interface carrying a sample mounted in between, wherein the sample is imaged by the microscope.

10. The autofocusing system of claim 3, wherein the imaging system comprises a microscope, wherein the objective element comprises an objective lens of the microscope and further wherein the optical interferometry system is positioned along the objective lens.

11. The autofocusing system of claim 3, wherein the optical interferometry system comprises a time domain, a spectral domain, or a swept source optical coherence tomography system.

12. The autofocusing system of claim 3, wherein the autofocusing system is operatively coupled to a super-resolution imaging system configured to perform inspection of a semiconductor device.

* * * * *